United States Patent [19]

Blair

[11] Patent Number: 4,649,108
[45] Date of Patent: Mar. 10, 1987

[54] ALPHA AMYLASE ASSAY

[75] Inventor: Henry E. Blair, Barnstable, Mass.

[73] Assignee: Genzyme Corporation, Boston, Mass.

[21] Appl. No.: 634,873

[22] Filed: Jul. 26, 1984

[51] Int. Cl.$^4$ .......................... C12Q 1/40; C12Q 1/66; C12Q 1/54; C12Q 1/34

[52] U.S. Cl. ......................................... 435/22; 435/8; 435/14; 435/18

[58] Field of Search .................. 435/8, 14, 18, 22, 810

[56] References Cited

U.S. PATENT DOCUMENTS

| | | | |
|---|---|---|---|
| 3,876,375 | 4/1975 | Maurukas | 23/230 |
| 4,102,747 | 7/1978 | Driscoll et al. | 435/22 |
| 4,145,527 | 3/1979 | Burns et al. | 536/4 |
| 4,147,860 | 4/1979 | Farnham et al. | 536/4 |
| 4,153,511 | 5/1979 | Modrovich | 536/27 |
| 4,233,403 | 11/1980 | Menson et al. | 435/22 |
| 4,250,254 | 2/1981 | Modrovich | 435/14 |
| 4,271,264 | 6/1981 | Modrovich | 435/14 |
| 4,277,562 | 7/1981 | Modrovich | 435/14 |
| 4,282,316 | 8/1981 | Modrovich | 435/12 |
| 4,310,625 | 1/1982 | Modrovich | 435/15 |
| 4,550,077 | 10/1985 | Woodbridge et al. | 435/22 |

FOREIGN PATENT DOCUMENTS 0104047 3/1984 European Pat. Off. .
2004646 4/1979 United Kingdom .

OTHER PUBLICATIONS

M. Matsui et al, "Research of Reactivity and Hydrolysis Type on Various Substrates for α-Amylase Assay by H.P.L.C.; Japan Clinical Chemistry Association Summer Seminar; Jul. 1982.
Marshall et al. (1977) New Serum alpha-Amylase Assay of High Sensitivity, Chimica Acta 76, 277–283.
Marshall, Analytical Biochemistry (1978) 85, 541–549.
Calbiochem–Behring (1981) Pantrak E.K. Amylase.
Biomedix (1980) Amylase (U.V.) DeltaTest Assay.

Primary Examiner—Robert J. Warden
Assistant Examiner—Patricia Kate White

[57] ABSTRACT

Method of measuring the amount of α-amylase in a liquid sample, including the steps of providing an oligosaccharide substrate for α-amylase, the substrate being characterized in that it contains at least 3 glucose units, its reducing-end glucose unit is bonded, via a bond cleavable by α- or β-glucosidase, to a label which exhibits an optically measurable change upon cleavage of the bond, and its terminal glucose unit is bonded to a blocking substituent which inhibits cleavage by exoenzymes of the bond between the terminal glucose unit and the adjacent glucose unit; contacting the sample with the oligosaccharide substrate and with a first exoenzyme capable of cleaving the bond between the reducing-end glucose unit and the label, and measuring the optically measurable change as a measure of α-amylase in the sample.

17 Claims, 2 Drawing Figures

ALPHA AMYLASE ASSAY

BACKGROUND OF THE INVENTION

This invention relates to measuring the enzyme α-amylase in biological fluids. The measurement of α-amylase in urine and serum is widely performed in the diagnosis of pancreatic disorders. A number of assay described in the literature employ oligosaccharide α-amylase substrates, which are cleaved into smaller chains by α-amylase (which is an endo-enzyme), in conjunction with an exo-enzyme, e.g., α-glucosidase, β-glucosidase, or glucoamylase.

Driscoll et al. U.S. Pat. No. 4,102,747 describes an assay employing oligosaccharides of chain length 4–10 glucose units, with a chromophore (p-nitrophenol, or "pNP") on the reducing end. The chain is "resistant to cleavage by α-glucosidase", and cleavage by α-amylase produces "smaller fragments which are acted upon by αglycosidase . . . to liberate p-nitrophenol."

Marshall et al. (1977) Clin Chimica Acta 277 describes an assay employing "modified amylaceous polysaccharides containing blockages to the action of glucoamylase. Such blockages to exo-enzyme action are conveniently introduced . . . by limited periodate oxidation . . . or by substitution of monosaccharide residues." "In the presence of excess glucoamylase, the amount of glucose released . . . is directly proportional to the amount of α amylase present." "Glucose was determined by the glucose oxidase method."

A brochure published by Calbiochem-Behring describes an assay, the "Pantrak® E. K. Amylase" method, similar to that of Driscoll et al., supra.

A biomedix® catalog describes the DeltaTest® Assay, similar to that of Marshall et al., supra.

Three patents assigned to E. I. DuPont de Nemours and Company (Burns et al. U.S. Pat. No. 4,145,527; Farnham et al. U.S. Pat. No. 4,147,860; and Menson et al. U.S. Pat. No. 4,233,403) describe assays similar to that of Driscoll et al., supra.

U.K. Pat. Appln. GB 2004646 describes an assay employing maltoheptaose as the α-amylase substrate.

SUMMARY OF THE INVENTION

In general, the invention features a method of measuring the amount of α-amylase in a liquid sample, including the steps of providing an oligosaccharide substrate for α-amylase, the substrate being characterized in that it contains at least 3 glucose units, it reducing-end glucose unit is bonded, via a bond cleavage by α- or β-glucosidase, to a label which exhibits an optically measurable change upon cleavage of the bond, and its terminal glucose unit is bonded to a blocking substituent which inhibits cleavage by exo-enzymes of the bond between the terminal glucose unit and the adjacent glucose unit; contacting the sample with the oligosaccharide substrate and with a first exo-enzyme capable of cleaving the bond between the reducing-end glucose unit and the label, and measuring the optically measurable change as a measure of α-amylase in the sample.

In preferred embodiments, the label is a chromophore, a fluorophore, a chemiluminescent substituent, or a bioluminescent substituent; the first exo-enzyme is α- or β-glucosidase or a mixture thereof; and the sample is also contacted with a second exo-enzyme, most preferably glucoamylase, whose action is independent of substrate chain length and which is incapable of cleaving the bond between the label and the reducing-end glucose unit. Preferred labels are p-nitrophenol, o-nitrophenol (chromophores), coumarin derivatives such as 4-methylumbelliferone (a fluorophore), and luciferin (a chemiluminescent substituent). Preferably, the substrate has eight of fewer glucose units, and most preferably has six or seven. Preferred blocking substituents are acetals or ketals, e.g., benzylidene. The reagents used in the assay are preferably provided in the form of a reagent kit, the reagents preferably being mixed together in a single container.

The assay of the invention works according to the following general scheme:

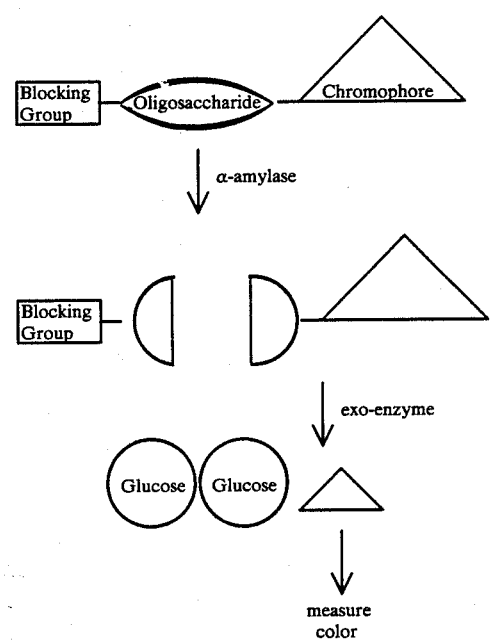

In the scheme illustrated above, the blocking group prevents exo-enzymes from breaking down the substrate, so that in the absence of α-amylase there will be no color change. α-Amylase, an endo-enzyme, cleaves interval α-1,4 bonds in the substrate, producing smaller fragments which can be acted on by the exo-enzyme, which causes the ultimate release of the chromophore.

The assay of the invention is most effective when two different exo-enzymes are used, particularly when the substrate contains more than four glucose units. The following scheme illustrates the action of α-amylase and two exo-enzymes, glycoamylase and α-glucosidase (in this scheme, there is an α-linkage between the chromophore and the reducing-end glucose unit; there could just as well be a β-linkage, in which case β-glucosidase could be used, or α- and β-linkages, in which case a mixture of the two enzymes could be used):

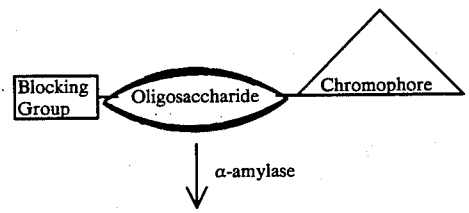

-continued

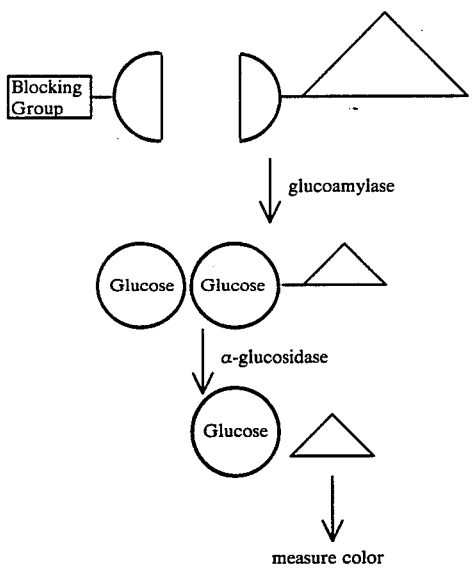

measure color

In the scheme illustrated above, the α-amylase acts as previously described. The two exo-enzymes, glucoamylase and α- or β-glucosidase, cooperate as follows. α- or β-glucosidase is relatively inactive during the period immediately following the initial cleavage of the substrate by α-amylase, because its activity is chain-length dependent, i.e., its activity is inversely proportional to substrate chain length. Glucoamylase, however, acts quickly to break the polysaccharide fragments into single glucose units, its activity being independent of chain length. As discussed above, neither enzyme can act until α-amylase has acted, because of the blocking group bonded to the terminal glucose unit. When the reducing-end glucose, with its chromophore, has been cleaved from the adjacent glucose unit, the role of glucoamylase is effectively completed, since glucoamylase cleaves only bonds between glucose units, and cannot cleave the bond between the reducing-end glucose and the chromophore. It is at this point that α- or β-glucosidase, which is capable of cleaving such bonds, plays its major role, by releasing measurable chromophore.

The assay of the invention produces a linear result, i.e., optical density (OD) measurements directly proportional to α-amylase concentration, following a very short lag time, rendering the assay highly susceptible to automation. Furthermore, the assay likely reduces susceptibility to inhibition by released glucose, because there is less released glucose present, since the portion of the oligosaccharide remaining blocked following the action of α-amylase remains inert to the exo-enzymes. In addition, the components of the assay can be provided in the form of a kit which has good stability in storage, because the blocking group prevents degradation of the substrate by α-glucosidase, which can otherwise degrade even long-chain substrates over time.

Other features and advantages of the invention will be apparent from the following description of the preferred embodiments thereof, and from the claims.

DESCRIPTION OF THE PREFERRED EMBODIMENTS

We first briefly describe the drawings.

Drawings

STRUCTURE AND SYNTHESIS OF SUBSTRATE

Figure 1:
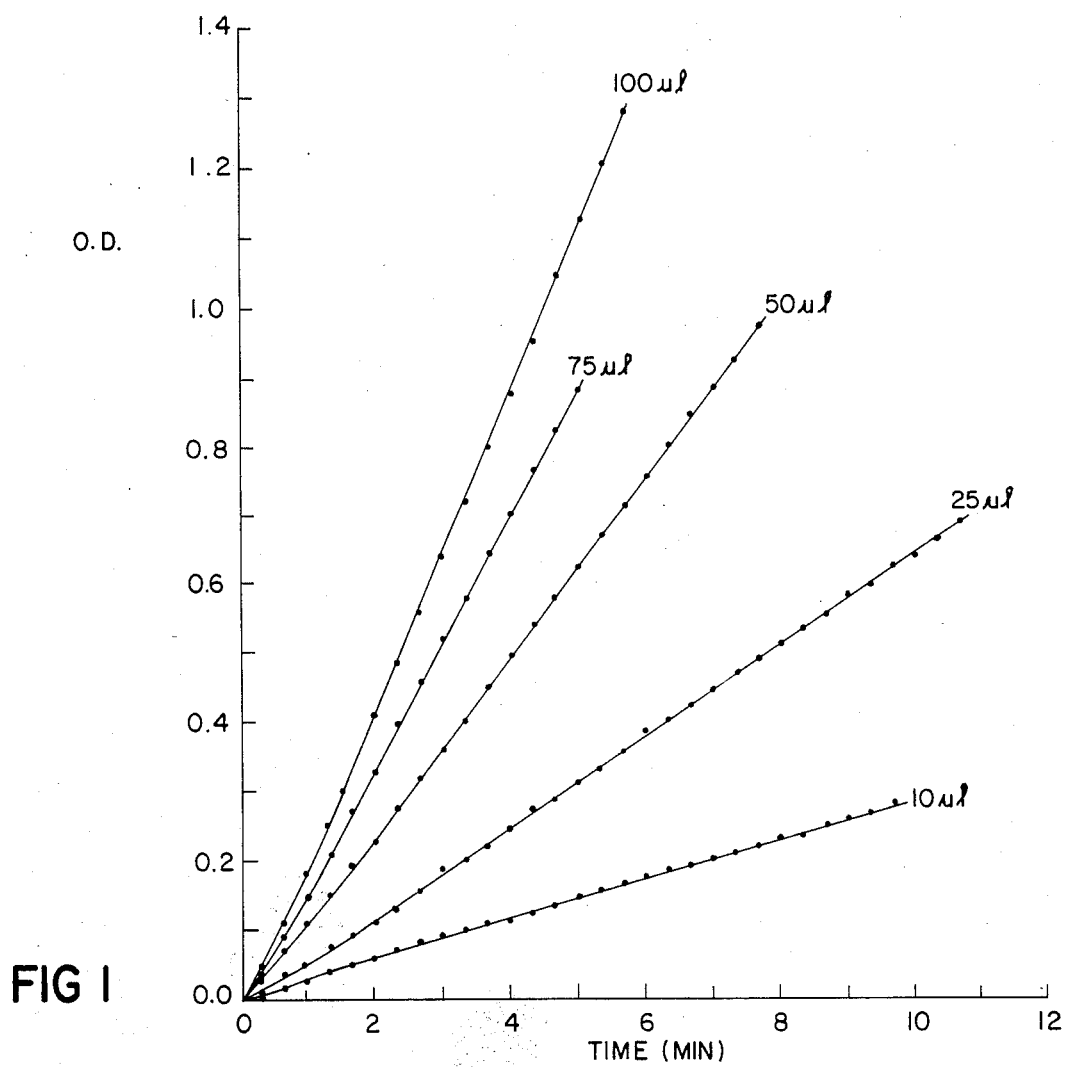
FIG. 1 is a graph of OD vs. time for five α-amylase standard samples, generated using an assay of the invention.

The oligosaccharide porton of the substrate can generally be obtained commercially, or can be synthesized using standard enzymic techniques, beginning with starch or cyclodextrins.

The label portion, preferably a chromophore such as p-nitrophenol or o-nitrophenol, or a fluorophore such as 4-methylumbelliferone, can be attached to the reducing-end glucose unit using standard techniques, e.g., those described in Driscoll et al. U.S. Pat. No. 4,102,747, hereby incorporated by reference having 4, 5, 6, and 7 glucose units, and oligosaccharide substrates labeled with p-nitrophenol are commercially available, e.g., from Cal Biochem Corporation.

The blocking group can be any substituent which prevents exo-enzymes from breaking down the substrate. The blocking group works by creating a terminal glucose unit no longer capable of fitting the active site of the exo-enzyme. Thus, the size and chemical composition of the blocking group are not critical; all that is required is that the lock-and-key enzyme/substrate interaction is prevented. Virtually any substituent bonded to C2, C3, C4, or C6 of the terminal glucose unit will block the action of exo-enzymes. Because the addition of blocking groups to C6 to easiest synthetically, C6 blockage (alone or in conjunction with blockage at C4) is preferred.

One class of blocking groups can replace a hydrogen in the hydroxyl group of C6 of the terminal glucose unit. Suitable such groups include, e.g., carboxylic acid esters (e.g., acetyl or benzoyl); phosphate esters; sulfonate esters (e.g., toluenesulfonyl or methanesulfonyl); ethers (e.g., benzyl, silyl, and triphenylmethyl); and monosaccharides other than α-1,4 linked glucose.

Alternatively, the blocking group can be an acetal or ketal blocking group, i.e., a group which blocks the C4 and C6 hydroxyls of the terminal glucose unit:

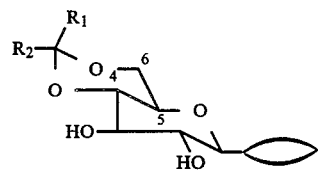

where (a) $R_1$ is H and $R_2$ is lower (5 or fewer carbon atoms) alkyl; lower (10 or fewer carbon atoms) aryl or aralkyl; or (b) $R_1$ is lower aryl or aralkyl or lower alkyl, and and $R_2$, independently, is lower aryl or aralkyl, lower alkyl, or $CO_2$—. In addition, blocking techniques such as those described in Marshall et al., supra, can be used.

Synthesis of a blocked substrate for use in the assay of the invention can be carried out according to either of the following general schemes; the illustrated chromophore is p-nitrophenol, the blocking group is benzylidene, and there are n+1 glycose units, where $2 \leq n \leq 7$:

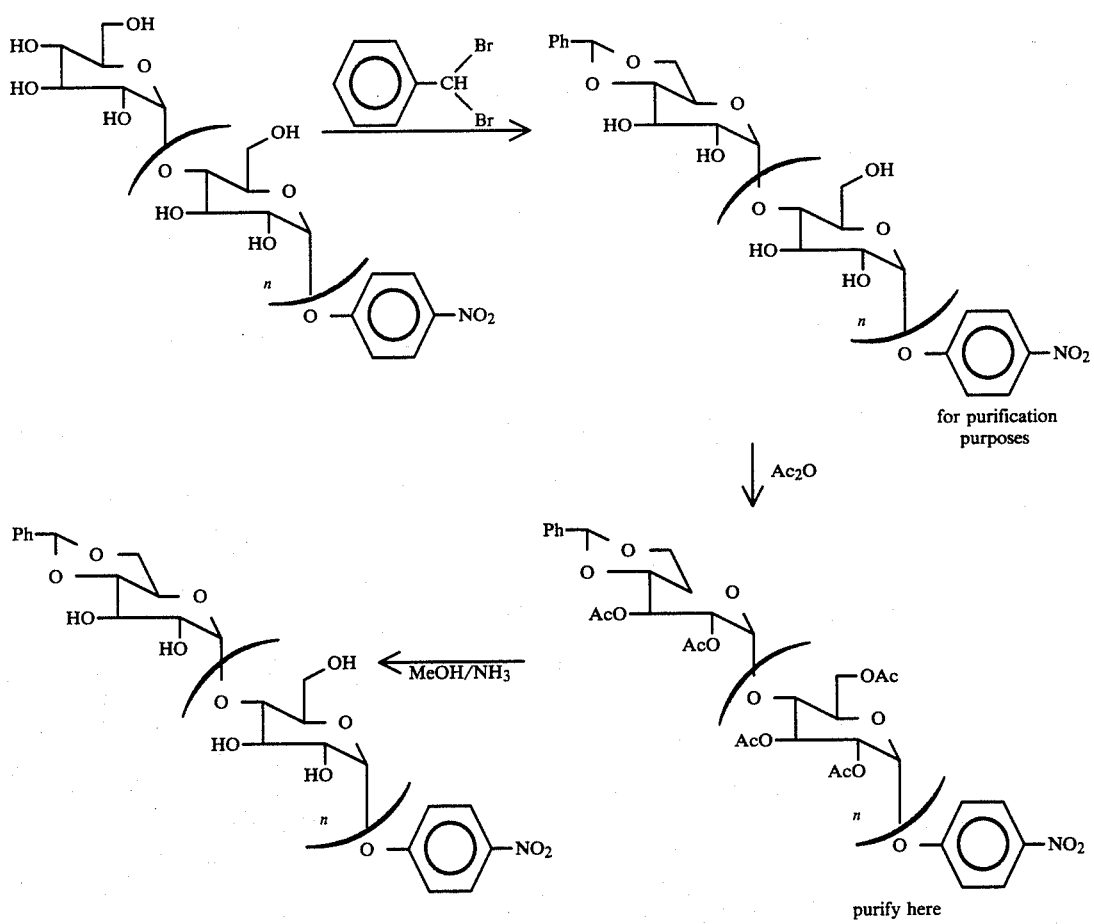

for purification purposes

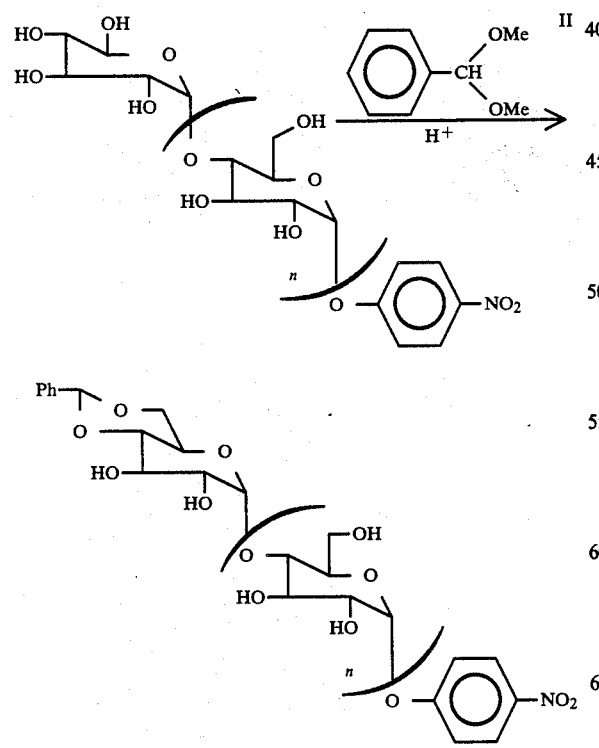

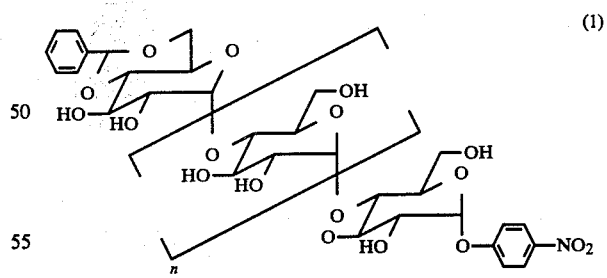

purify here

A substrate containing six glucose units, blocked with benzylidene and labeled with p-nitrophenol, has the formula O-(4,6-O-benzylidene-α-D-glucopyranosyl)-(1-4)-O-(α-D-glucopyranosyl)-(1-4)-O-(α-glucopyranosyl)-(1-4)-O-(α-D-glucopyranosyl)(1-4)-O-(α-glucopyranosyl)-(1-4)-O-(4-nitrophenyl-O-α-D-glucopyranoside), and the structure:

(1)

where n=4.

Compound (1) was synthesized using general method I, as follows. To 2 ml of freshly dried and distilled pyridine was added 39 mg (0.035 mmol) of α-(4-nitrophenyl)maltohexaoside. The temperature was raised to 40° C. and stirring was continued until all material had dissolved (about 15 min.). The reaction vessel was degassed with argon (3 evacuation-purge cycles), and then a portion of dried and distilled benzal bromide (4 μL, 0.67 equiv.) was added. The temperature was gradually (over 30 min.) increased to 115° C. After 3 h at 115° C.

an additional 4 μL (0.67 equiv.) of benzal bromide was added. A final 4 μL (0.67 equiv.; 2.0 equiv. total) of benzal bromide was added 2.5 h later. The mixture was heated at 115° C. for an additional 2 h, and then was cooled in a 0° C. ice bath. After excess acetic anhydride (1 mL) was added, the reaction mixture was allowed to warm to room temperature and stirred until the acylation was complete as judged by analytical TLC (typically 24–48 h). The solution was then diluted with 15 mL of saturated aqueous $NaHCO_3$. The aqueous phase was extracted with 10 ml portions of $CHCl_3$ (5x). The combined organic layers were washed with saturated aqueous $NaHCO_3$ (10 ml) and filtered through adsorbent cotton. After evaporative removal of the $CHCl_3$ the remaining pyridine was removed by azeotropic evaporation with several portions of EtOH. A final trituration with EtOH (2 ml) removed any remaining pyridine and left a crude yellow solid. The crude product was purified by preparative thin layer chromatography on two 500μ silica gel plates (96:4 benzene-methanol eluant) to give 24.2 mg (36%) of chromatographically homogeneous material ($R_f$ 0.18). Peracylated α-(4-nitrophenyl)maltohexaoside (that is, acylated starting material) was also present ($R_f$ 0.13) but was not recovered. Recrytallization from anhydrous EtOH yielded 21.2 mg of analytically pure compound (2).

The product of this reaction had the formula O-(2,3-Di-O-acetyl-4,6-O-benzylidene-α-D-glycopyranosyl)-(1-4)-O-(2,3,6-tri-O-acetyl-α-D-glucopyranosyl)-(1-4)-O-(2,3,6-tri-O-acetyl-α-D-glucopyranosyl)-(1,4)-O-(2,3,6-tri-O-acetyl-α-D-glucopyranosyl)-(1-4)-O-(2,3,6-tri-O-acetyl-α-D-glucopyranosyl)-(1-4)-O-(2,3,6-tri-O-acetyl-4-nitrophenyl-O-α-D-glucopyranoside), and the structure

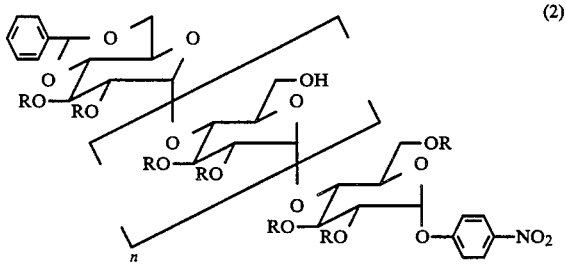

(2)

where n=4, and R=Ac.

Compound (1) was prepared from compound (2) as follows. A solution of compound (2) in 2.0 mL of $CH_3OH$ was treated with 2.0 mL of a saturated $NH_3$ in $CH_3OH$ solution. The resultant mixture was stirred at ambient temperature for 21 h. After evaporative removal of the $NH_3/CH_3OH$ and one trituration with ether 12.2 mg (100%) of solid compound (1) was obtained. This material was not purified further. Enzymic analysis suggested that this sample contained about 8% of free p-nitrophenylmaltohexoside.

α-Amylase Assay

A substrate solution was prepared by dissolving 12 mg of compound (1), above, in 12 ml of 50 mM αβDL glycerol $PO_4$, pH 7.0 ("Gly $PO_4$" buffer). α-Glucosidase in 25% glycerol (1,975 units/ml) was obtained from the DuPont Company and glucoamylase was obtained from the Nova Company, purified by conventional methods, and reconstituted in distilled water to yield 100 units/ml working solution. The α-amylase used as a standard was Sigma Enzyme Control 2E.

Individual 1 cm path length cuvettes were made up containing 0.9 ml substrate solution, 0.0127 ml α-glucosidase stock solution, and 0.10 ml glucoamylase stock solution. The cuvettes were preincubated at 37° C. in a continuous recording spectrophotometer, and the α-amylase standard was then added to each cuvette and ΔOD monitored at 405 nM. The results, from the linear portion (after about 2½ min), are summarized in the following table:

| Volume of Sigma E 2 Standard Added: | Δ O.D. per minute: | Total Volume: | Δ O.D. per min. × Volume: |
|---|---|---|---|
| 10 μl | 0.028 | 1.023 ml | 0.029 |
| 25 μl | 0.066 | 1.038 ml | 0.069 |
| 50 μl | 0.132 | 1.063 ml | 0.140 |
| 75 μl | 0.184 | 1.088 ml | 0.200 |
| 100 μl | 0.231 | 1.113 ml | 0.257 |

Figure 2:
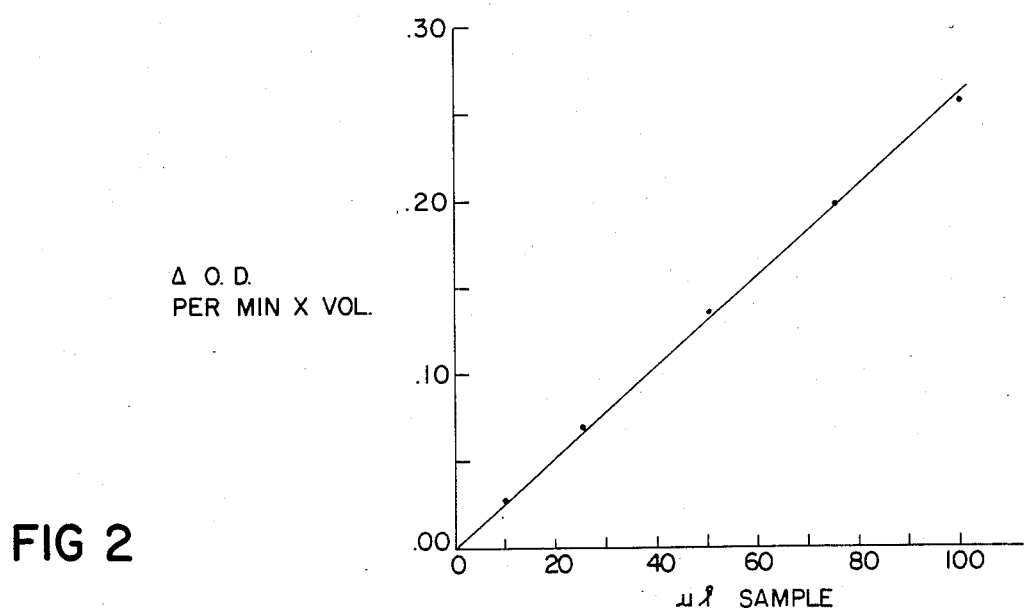
FIG. 2 is a graph of OD per min. times total assay vol. vs. sample volume, generated using an assay of the invention.

The data from the above table were used to generate the graphs of FIGS. 1 and 2. FIG. 1 shows a substantially linear relationship between amount of α-amylase and ΔOD, only 1-2 min. following the initiation of the reaction, at five volumes. The graph of FIG. 2 is corrected for volume and shows that the linear relationship holds, between enzyme concentration and ΔOD.

Reagent Kit

The reagents used in the assay method of the invention are preferably provided in the form of a reagent kit which includes the following components, admixed in a single container e.g., a glass bottle:

Blocked, labeled substrate (preferably containing 6 or 7 glucose units)
Glucoamylase
α- or β-glucosidase
Activator (preferably a source of Cl⁻ ion, e.g., NaCl or KCl, at a concentration of about 50 mM)
Buffer (e.g., PIPES or HEPES, at a concentration of about 50 mM)
An anti-glucose interference agent (preferably hexokinase [~10 units/ml], ATP [~5 mg/ml], and $MgCl_2$ [~10 mM].

Substrate, glucoamylase, and α- and/or β-glucosidase are used in amounts comparable to those used in prior α-amylase assays. The remaining listed ingredients are conventional.

To assay a sample of urine or serum for α-amylase, water and sample are added to the reagent kit, and optical density or fluorescence are measured and compared to standards.

Other embodiments are within the following claims.

I claim:

1. A method of measuring the amount of α-amylase in a liquid sample comprising the steps of
providing an oligosaccharide substrate for α-amylase, said substrate being characterized in that
it contains at least 3 glucose units,
the reducing-end glucose unit is bonded, via a bond cleavable by α- or β-glucosidase, to a label which exhibits an optically measurable change upon cleavage of said bond, and
the terminal glucose unit is bonded to a chemical blocking substituent which inhibits cleavage by exo-enzymes of the bond between said terminal glucose unit and the adjacent glucose unit,
contacting said sample with said oligosaccharide substrate and with a first added exo-enzyme capable of cleaving the bond between said reducing-end glucose unit and said label, and a second added exo-enzyme, capable of cleaving bonds between glucose units, to form a mixture comprising said substrate, said first exo-enzyme, and said second exo-enzyme and measuring said optically measurable change as a measure of said α-amylase in said sample.

2. The method of claim 1 wherein said label is a chromophore, a fluorophore, a chemiluminescent substituent, or a bioluminescent substituent.

3. The method of claim 2 wherein said chromophore comprises p-nitrophenol or o-nitrophenol.

4. The method of claim 2 wherein said fluorophore comprises a coumarin derivative.

5. The method of claim 4 wherein said coumarin derivative comprises 4-methylumbelliferone.

6. The method of claim 1 wherein said first exo-enzyme comprises α-glucosidase.

7. The method of claim 1 wherein said first exo-enzyme comprises α-glucosidase.

8. The method of claim 1 wherein said first exo-enzyme comprises a mixture of α-glucosidase and β-glucosidase.

9. The method of claim 1 wherein the activity of said second exo-enzyme is independent of substrate chain length and wherein said second enzyme is not capable of cleaving said bond between said label and said reducing-end glucose unit.

10. The method of claim 1 wherein said second exo-enzyme comprises glucoamylase.

11. The method of claim 1 wherein said first and said second exo-enzymes are contacted with said sample at the same time.

12. The method of claim 1 wherein said first exo-enzyme comprises α- or β-glucosidase and said secon exo-enzyme comprises glucoamylase.

13. The method of claim 1 wherein said label comprises luciferin.

14. The method of claim 1 wherein said blocking substituent comprises benzylidene.

15. The method of claim 1 wherein said substrate contains eight or fewer glucose units.

16. The method of claim 15 wherein said substrate contains six glucose units.

17. The method of claim 15 wherein said substrate contains seven glucose units.

* * * * *

UNITED STATES PATENT AND TRADEMARK OFFICE
CERTIFICATE OF CORRECTION

PATENT NO. : 4,649,108
DATED : March 10, 1987
INVENTOR(S) : Henry E. Blair

It is certified that error appears in the above-identified patent and that said Letters Patent are hereby corrected as shown below:

Column 1, line 20; "αglycosidase" is changed to --α-glucosidase--.

Column 1, line 29; "α amylase" is changed to --α-amylase--.

Column 1, line 49; "it" (second occurance) is changed to --its--.

Column 6, line 42; "(α-D-glucopyranosyl[1-4)-O-" is changed to

--(α-D-glucopyranosyl)-(1-4)-O--.

Column 9, line 21 (claim 7, line 2)

" α-glucosidase" is changed to --β-glucosidase--.

Column 10, line 12 (claim 12, line 2)

"secon" is changed to --second--.

Signed and Sealed this

Twenty-fourth Day of November, 1987

Attest:

DONALD J. QUIGG

Attesting Officer

Commissioner of Patents and Trademarks